US00PP16135P2

(12) United States Plant Patent
Toyama

(10) Patent No.: US PP16,135 P2
(45) Date of Patent: Nov. 29, 2005

(54) CHERRY TREE NAMED 'PC7064-3'

(50) Latin Name: *Prunus avium*
Varietal Denomination: PC7064-3

(75) Inventor: Thomas K. Toyama, Eugene, OR (US)

(73) Assignee: Washington State University Research Foundation, Pullman, WA (US)

( * ) Notice: Subject to any disclaimer, the term of this patent is extended or adjusted under 35 U.S.C. 154(b) by 193 days.

(21) Appl. No.: 10/402,323

(22) Filed: Mar. 27, 2003

Related U.S. Application Data

(60) Provisional application No. 60/368,656, filed on Mar. 28, 2002.

(51) Int. Cl.[7] ..... A01H 5/00
(52) U.S. Cl. ..... Plt./181
(58) Field of Search ..... Plt./181

*Primary Examiner*—Bruce R. Campell
*Assistant Examiner*—S. B. McCormick-Ewoldt
(74) *Attorney, Agent, or Firm*—Stratton Ballew PLLC

(57) ABSTRACT

A new cultivar of sweet cherry (*Prunus avium*), named 'PC7064-3' is disclosed. The new cultivar is notable for its very large, high quality dark red fruit.

2 Drawing Sheets

Latin name of the genus and species of the plant claimed: *Prunus avium.*

Variety denomination: PC7064-3.

BACKGROUND OF THE INVENTION

The new cherry tree 'PC7064-3' was developed as part of a controlled breeding program at the Washington State University Irrigated Agriculture Research and Extension Center at Prosser, Wash. It was selected from among several seedlings of the variety 'P8-79' (unpatented variety)×'Stella' (unpatented variety) from crosses made in 1970, and was subsequently asexually propagated by chip budding at Prosser. Asexual propagation of 'PC7064-3' has shown that its desirable characteristics reproduce true to form and are established and transmitted through succeeding generations.

'PC7064-3' is notable for its very large, high quality dark red fruit, which are larger than the fruit of male parent 'Stella' and ripen later than 'Stella.' Bloom time for the new cultivar is approximately the same as for 'Bing'; the fruit of the new cultivar ripens about the same time as 'Lapins.' 'PC7064-3' is self fertile. All closely observed second and third generation test trees have shown no tendency toward the cherry crinkle-leaf disorder that is common in 'Bing' as well as in several other varieties of sweet cherry.

DETAILED BOTANICAL DESCRIPTION

Figure 1:
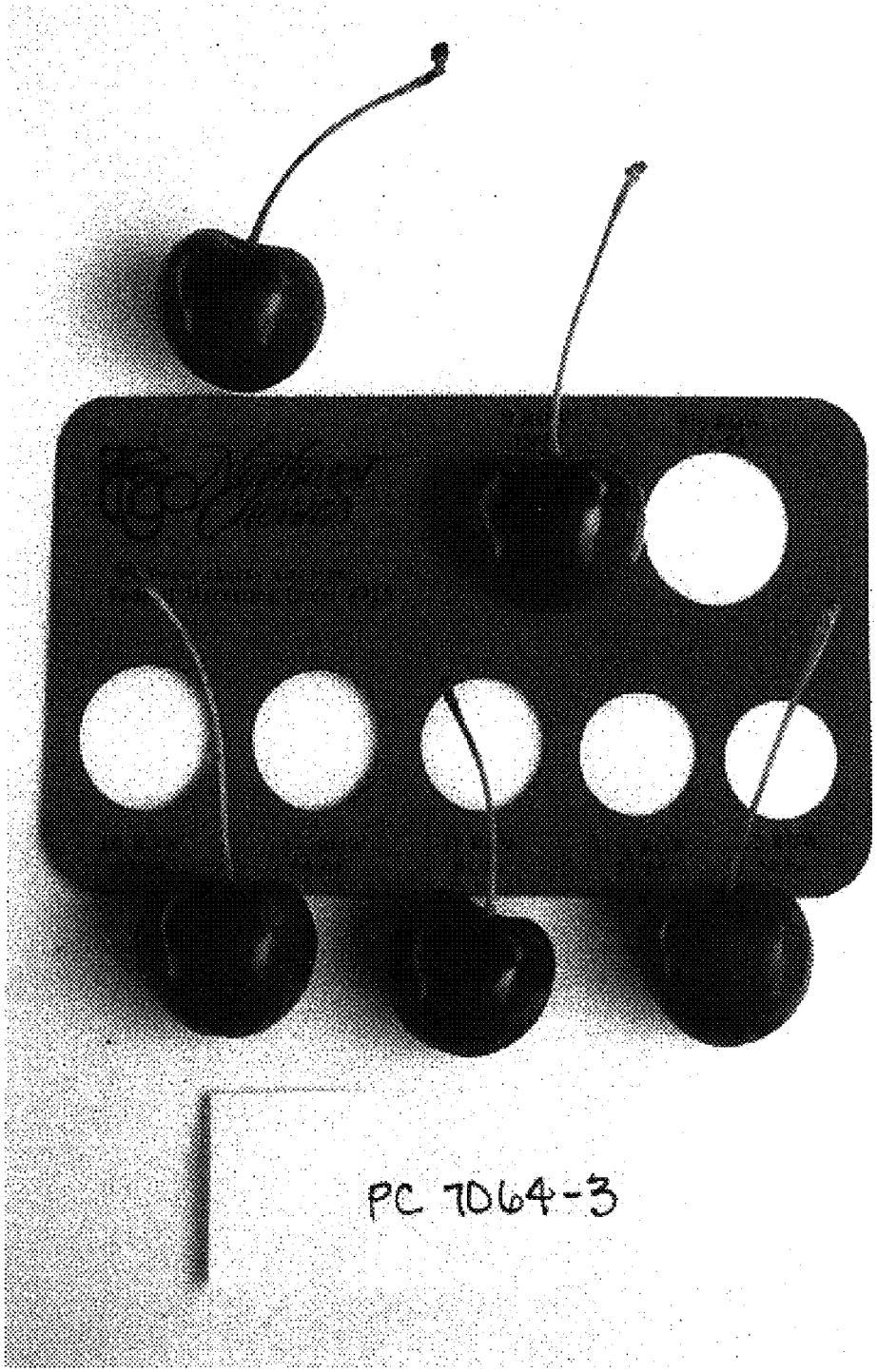
FIG. 1 is a color photograph showing the fruit of the new cultivar.
Figure 2:
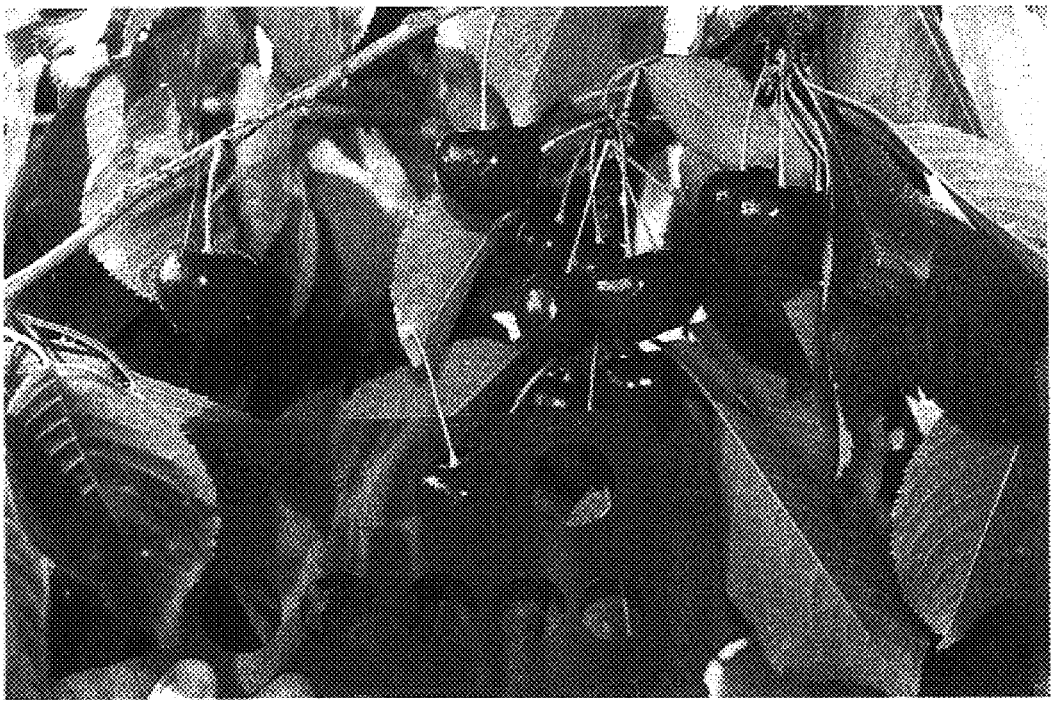
FIG. 2 is a color photograph showing fruit and leaves of the new cultivar.

The following is a detailed botanical description of the new and distinct variety of *Prunus avium* named 'PC7064-3', based on observations made during the 2002 growing season of 24-year old specimen trees grown near Prosser, Wash. The specimen trees were grown on 'Mazzard' (unpatented) rootstock. It should be understood that the botanical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Color designations are made in reference to The Royal Horticultural Society Colour Chart.

Tree:

*Size.*—Large. Average size 14 feet high, 18 feet wide (on 'Mazzard' rootstock).

*Vigor.*—Vigorous. Average growth 18 inches per year.

*Branching habit.*—Upright-spreading.

*Density.*—Average for sweet cherry.

*Form.*—Round-headed when mature.

*Hardiness.*—Hardy in area where tested.

*Production.*—More productive than 'Bing' or 'Lapins'.

*Bearing.*—Consistent, regular.

Trunk:

*Size.*—Stocky, average 42.7 cm diameter.

*Bark texture.*—Mixed; some smooth and some rough areas; some rough areas peel away from trunk; typical for sweet cherry.

*Bark color.*—Gray brown; smooth areas 187A, rough areas 197A.

*Lenticels.*—Numerous; Large, average 3–20 mm diameter; greyed-green 197B.

Branch:

*Size.*—Stocky main scaffolds as large as 21.4 cm diameter; fruiting branches vary.

*Crotch angle of bearing branches.*—25°–90° from vertical.

*Texture.*—Average, typical for sweet cherry.

*Color.*—First year wood, light green 143C; Second year wood, grey-brown N199B.

*Lenticels.*—Numerous; Medium, average 1–3 mm in diameter; greyed-orange 177C.

Leaves: (Measurements are from mature leaves attached at midpoint of actively growing upright shoots of current season's growth.).

*Size.*—Very large, average 14–16 cm long, 7–8 cm wide.

*Arrangement.*—Typical of species.

*Form.*—Lanceolate with acuminate tip.

*Margin.*—Serrulate.

*Venation.*—Pinnate.

*Color.*—Upper surface, glossy green 132A; Lower surface, light green 132D.

*Midvein.*—Large, average 1.5 mm diameter; Green 141D.

*Petiole.*—Medium to short, average 30–35 mm long, 2–3 mm thick; green 141D.

*Glands.*—2; Large, 2 to 3 mm long, oval.

Flower:

*Bloom date.*—Approximately April 5 to April 23; average April 15.

*Dormant buds.*—7.3 to 9.4 mm long, average 8.1 mm; 2.6 to 4.0 mm wide, average 3.3 mm; color greyed-orange 177A.

Fruit:

*Maturity.*—Eating ripe June 28 (16 year average).

*Date of first picking.*—June 17.

*Date of last picking.*—July 12.

*Size.*—Very large, average 8–13 g; diameter transversely across suture, average 2.5–2.9 cm; diameter apically average 2.2–2.5 cm.

*Form.*—Uniform; symmetrical.

*Suture.*—Very shallow.

*Stem.*—Long, thin, average 4–5 cm in length; Light green 141D.

*Skin.*—Medium thickness; Medium texture (neither exceptionally smooth nor rough); Tenacious to flesh; Susceptible to cracking caused by prolonged rains, about the same as 'Bing'; No susceptibility to cracking in dry season; Color, red 53B, red-purple 59A.

*Flesh.*—Color, red 45A; Texture, firm, crisp; Eating quality, good.

*Stone.*—Semi-free stone; Small, average 1 cm long, 0.8 cm wide; Oval; color greyed-orange 164C.

Use: Late season shipping to fresh markets.

Keeping quality: Good.

Resistance to insects and diseases: Susceptible to bacterial canker (pseudomonas); no cherry crinkle-leaf noted.

Shipping quality: Firm.

I claim:

1. A new and distinct cherry tree, substantially as shown and described herein.

* * * * *